United States Patent
Suzuki et al.

(10) Patent No.: US 8,442,629 B2
(45) Date of Patent: May 14, 2013

(54) IONTOPHORESIS PREPARATION FOR TREATING BREAST CANCER AND/OR MASTITIS

(75) Inventors: Kenichi Suzuki, Fuji (JP); Makoto Kanebako, Fuji (JP); Toshio Inagi, Fuji (JP)

(73) Assignee: Kowa Co., Ltd., Nagoya-shi (JP)

( * ) Notice: Subject to any disclaimer, the term of this patent is extended or adjusted under 35 U.S.C. 154(b) by 277 days.

(21) Appl. No.: 12/988,047

(22) PCT Filed: Apr. 17, 2009

(86) PCT No.: PCT/JP2009/001770
§ 371 (c)(1),
(2), (4) Date: Oct. 15, 2010

(87) PCT Pub. No.: WO2009/128273
PCT Pub. Date: Oct. 22, 2009

(65) Prior Publication Data
US 2011/0034859 A1    Feb. 10, 2011

(30) Foreign Application Priority Data
Apr. 18, 2008  (JP) ................................. 2008-108754

(51) Int. Cl.
*A61N 1/30*  (2006.01)
*A61K 33/00*  (2006.01)

(52) U.S. Cl.
USPC .............................. 604/20; 424/661; 424/722

(58) Field of Classification Search ..... 604/20; 424/661, 424/722
See application file for complete search history.

(56) References Cited

U.S. PATENT DOCUMENTS

| | | | |
|---|---|---|---|
| 7,384,418 B2 * | 6/2008 | Hung et al. | 604/890.1 |
| 8,034,824 B2 | 10/2011 | Inagi et al. | |
| 2003/0216661 A1 * | 11/2003 | Davies | 600/547 |
| 2004/0152997 A1 * | 8/2004 | Davies | 600/547 |
| 2004/0229813 A1 | 11/2004 | DiPiano et al. | |
| 2004/0253652 A1 * | 12/2004 | Davies | 435/7.23 |
| 2004/0258747 A1 | 12/2004 | Ponzoni et al. | |
| 2004/0267189 A1 * | 12/2004 | Mavor et al. | 604/20 |
| 2005/0203436 A1 * | 9/2005 | Davies | 600/547 |
| 2006/0177449 A1 | 8/2006 | Matsumoto et al. | |
| 2006/0184092 A1 * | 8/2006 | Atanasoska et al. | 604/20 |

FOREIGN PATENT DOCUMENTS

| | | |
|---|---|---|
| EP | 1 008 365 A1 | 6/2000 |
| JP | 2004-300147 | 10/2004 |
| JP | 4000185 | 8/2007 |
| WO | 98 35722 | 8/1998 |

(Continued)

OTHER PUBLICATIONS
U.S. Appl. No. 13/204,803, filed Aug. 8, 2011, Inagi, et al.

(Continued)

*Primary Examiner* — Kevin C Sirmons
*Assistant Examiner* — Michael J Anderson
(74) *Attorney, Agent, or Firm* — Oblon, Spivak, McClelland, Maier & Neustadt, L.L.P.

(57) ABSTRACT

Provided is to enhance the therapeutic effect of an iontophoretic preparation for treatment of breast cancer or mastitis. An iontophoretic preparation for treatment of breast cancer and/or mastitis containing, as an active ingredient, a nonsteroidal anti-inflammatory analgesic agent and/or an anticancer agent, wherein an electrolyte is topically administered through the nipple part into the mammary gland; subsequently, a donor is applied to the nipple part; and the active ingredient is topically administered through the nipple part into the mammary gland by application of current.

10 Claims, 1 Drawing Sheet

FOREIGN PATENT DOCUMENTS

| WO | WO 98/35722 | 8/1998 |
|---|---|---|
| WO | WO 2004/060322 A2 | 7/2004 |
| WO | WO 2004/105782 A2 | 12/2004 |
| WO | 2005 103186 | 11/2005 |
| WO | 2007 043580 | 4/2007 |

OTHER PUBLICATIONS

Office Action mailed Apr. 14, 2010, in co-pending U.S. Appl. No. 12/089,804.

David L. McCormick, et al., "Modulation of Rat Mammary Carcinogenesis by Indomethacin[1]", Cancer Research, vol. 45, Apr. 1985, pp. 1803-1808.

Pamela Harrison, "Low-Dose Topical 5-Fluorouracil As Effective, Better Tolerated Than Standard 5% Cream: Presented at AAD", Doctor'S Guide, http://docguide.com/news/content.nsf/NewsPrint, Feb. 26, 2002, pp. 1-2.

W. J. L. Jack, et al., "Adjuvant Therapy with 5-Fluorouracil for Breast Cancer of Likely Poor Prognosis: 15-Year Results of a Randomized Trial", Clinical Oncology, 1995, pp. 7-11.

Garth Powis, et al., "Effect of body weight on the pharmacokinetics of cyclophosphamide in breast cancer patients", Cancer Chemotherapy and Pharmacology, vol. 20, 1987, pp. 219-222.

Ayumi Denda, et al., "COX-2 and Cancer Prevention", Journal of Clinical and Experimental Medicine, vol. 204, No. 1, 2003, pp. 10-19 (with partial English translation).

Makoto M. Taketo, "Cyclooxygenase-2 Inhibitors in Tumorigenesis (Part II)", Journal of the National Cancer Institute, vol. 90, No. 21, Nov. 4, 1998, pp. 1609-1620.

Yang Cao, et al., "Many Actions of Cyclooxygenase-2 in Cellular Dynamics and in Cancer", Journal of Cellular Physiology 190, 2002, pp. 279-286.

Marco E. Turini, et al., "Cyclooxygenase-2: A Therapeutic Target", Annual Review Medicine, 53, 2002, pp. 35-57.

Ayumi Denda, et al., "Increased expression of cyclooxygenase-2 protein during rat hepatocarcinogenesis caused by a choline-deficient, $_L$-amino acid-defined diet and chemopreventive efficacy of a specific inhibitor, nimesulide", Carcinogenesis, vol. 23, No. 2, 2002, pp. 245-256.

Yoshiko Ohtaka, et al., "Mastitis and Breast-feeding", Perinatal Medicine, vol. 34, No. 9, 2004-9, pp. 1443-1445 (with partial English translation).

Kiyofumi Katayama, "Fundamental and Clinical Study of the Local Therapy of the Breast Cancer", Journal of Yokohama Medical Association, vol. 44, 1993, pp. 487-494 (with English Abstract).

Dermatology and Venereology, vol. V, No. 2, Feb. 1951, p. 65.

International Search Report issued May 26, 2009 in PCT/JP09/01770 filed Apr. 17, 2009.

Yamamura, Takahiro et al., "Study on the Effect of Pre-Iontophoresis on Promotion of Transdermal Drug Penetration", The $12^{TH}$ APSTJ Annual Meeting Koen Yoshishu, pp. 206 to 207, (Mar. 14, 1997), (with English translation).

Inagi, Toshio: "Development of the Breast Cancer Cure by Using Iontophoretic Method", Journal of Pharmaceutical Science and Technology, vol. 67, No. 3, pp. 193-197, (2007), (with English translation).

* cited by examiner

IONTOPHORESIS PREPARATION FOR TREATING BREAST CANCER AND/OR MASTITIS

CROSS-REFERENCE TO RELATED APPLICATIONS

This application is a National Stage of PCT/JP09/001770 filed Apr. 17, 2009 and claims the benefit of JP 2008-108754 filed Apr. 18, 2008.

TECHNICAL FIELD

The present invention relates to an iontophoretic preparation for treatment of breast cancer and/or mastitis; and to an iontophoretic therapy for breast cancer and/or mastitis.

BACKGROUND ART

Breast cancer, which occurs in mammary tissue, is classified into lobular carcinoma arising from acini and breast ductal carcinoma arising from breast ducts. Noninfiltration breast cancer represents the state where cancer is limited within lobules or breast ducts, and cancer cells are not disseminated to surrounding tissues, whereas infiltration breast cancer represents the state where cancer cells proliferated in breast ducts destroy the basement membrane and metastasize to surrounding tissues. Adjuvant chemotherapy is an ordinary method for the treatment of breast cancer, in which an anticancer agent is administered by infusion without surgery, or after excision of an affected portion through surgery. However, many anticancer agents pose problems in that, when administered by infusion, they may cause side effects such as nausea, anorexia, and alopecia.

Mastitis is classified into stagnation mastitis and acute suppurative mastitis. Stagnation mastitis represents the state where breast ducts are congested with milk, and develops immediately after puerperium. Meanwhile, acute suppurative mastitis develops through infection with a bacterium such as *Staphylococcus*, *Escherichia coli*, or *Streptococcus*. Of these types of mastitis, acute suppurative mastitis has been treated with an anti-inflammatory analgesic agent.

However, such a treatment poses a problem in that a nonsteroidal anti-inflammatory analgesic agent and/or an anticancer agent cannot be administered topically, since breast cancer or mastitis occurs or develops in the breast.

Then, the present inventors conducted studies by focusing on iontophoresis, which has been known as means for enhancing percutaneous absorption, and found that when a donor of an iontophoretic preparation containing a nonsteroidal anti-inflammatory analgesic agent and/or an anticancer agent is applied to the nipple part and current is applied thereto, the topical delivery of such an active ingredient into the mammary gland is drastically improved, as compared with the case where the donor is applied to a normal skin area (e.g., a skin area of the breast) and current is applied thereto, and therefore such an iontophoretic approach is useful as means for the treatment of breast cancer and/or mastitis through topical administration. The inventors previously filed a patent on the basis of this finding (Patent Document 1).

PRIOR ART DOCUMENT

Patent Document

Patent Document 1: Japanese Patent No. 4000185

Non-Patent Document

Non-Patent Document 1: Journal of Pharmaceutical Science and Technology, Japan Vol. 57, April 1997 Supplement, pp. 206-207

SUMMARY OF THE INVENTION

Problems to be Solved by the Invention

An object of the present invention is to provide means for further enhancing the therapeutic effect of the aforementioned iontophoretic preparation for the treatment of breast cancer or mastitis.

Means for Solving the Problems

In order to improve the topical delivery of an active ingredient through the nipple part into the mammary gland by means of the aforementioned iontophoretic preparation, the present inventors have conducted studies, and have found that when, firstly, an electrolyte is topically administered through the nipple part into the mammary gland, and subsequently an active ingredient is topically administered through the nipple part into the mammary gland by application of current, the percent delivery of the active ingredient into the mammary gland is remarkably enhanced, and the delivery rate of the active ingredient is enhanced, as compared with the case where the active ingredient is topically administered directly through the nipple part into the mammary gland by application of current. The present invention has been accomplished on the basis of this finding.

Accordingly, the present invention provides an iontophoretic preparation for treatment of breast cancer and/or mastitis comprising, as an active ingredient, a nonsteroidal anti-inflammatory analgesic agent and/or an anticancer agent, wherein an electrolyte is topically administered through the nipple part into the mammary gland; subsequently, a donor is applied to the nipple part; and the active ingredient is topically administered through the nipple part into the mammary gland by application of current.

The present invention also provides use of a combination of an electrolyte and a nonsteroidal anti-inflammatory analgesic agent and/or an anticancer agent for producing an iontophoretic preparation for treatment of breast cancer and/or mastitis, wherein the electrolyte is topically administered through the nipple part into the mammary gland; subsequently, a donor is applied to the nipple part; and the nonsteroidal anti-inflammatory analgesic agent and/or the anticancer agent as an active ingredient is topically administered through the nipple part into the mammary gland by application of current.

The present invention also provides an iontophoretic therapy for breast cancer and/or mastitis, which comprises topically administering an electrolyte through the nipple part into the mammary gland; subsequently applying, to the nipple part, a donor containing, as an active ingredient, a nonsteroidal anti-inflammatory analgesic agent and/or an anticancer agent; and topically administering the active ingredient through the nipple part into the mammary gland by application of current.

Effects of the Invention

According to the present invention, a larger amount of a nonsteroidal anti-inflammatory analgesic agent and/or an anticancer agent (i.e., an active ingredient) can be rapidly absorbed specifically in the mammary gland, as compared with the case where only such an active ingredient is directly delivered into the mammary gland by application of current. Therefore, the present invention realizes treatment of breast cancer and/or mastitis with a smaller dose, as compared with conventional cases, and therefore can reduce side effects.

DESCRIPTION OF REFERENCE NUMERALS

Figure 1:
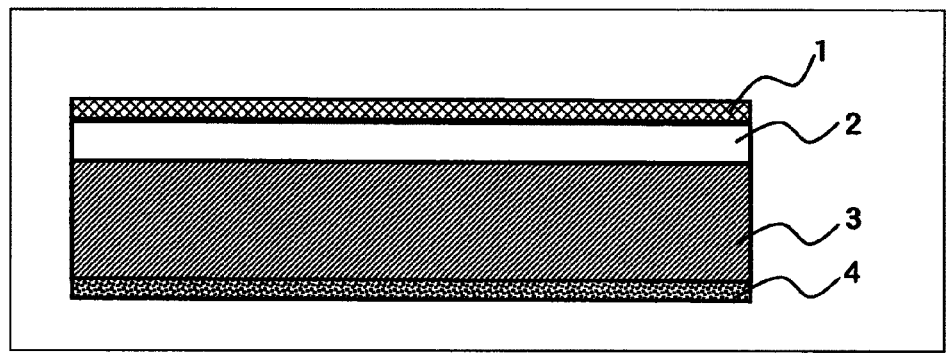
FIG. 1 is a schematic cross-sectional view of the iontophoretic preparation for treatment of breast cancer and/or mastitis of the present invention.

1: Support
2: Electrode
3: Pad
4: Liner

MODES FOR CARRYING OUT THE INVENTION

In the iontophoretic therapy for breast cancer and/or mastitis of the present invention, firstly, an electrolyte is topically administered through the nipple part into the mammary gland; subsequently, a donor is applied to the nipple part; and an active ingredient is topically administered through the nipple part into the mammary gland by application of current. Unexpectedly, when an electrolyte is topically administered through the nipple part into the mammary gland before administration of an active ingredient through the nipple part by application of current (hereinafter, topical administration of an electrolyte before administration of an active ingredient may be referred to as "preliminary treatment"), the topical delivery of the active ingredient from the nipple part into the mammary gland and the delivery rate thereof are remarkably enhanced. As has been known, when, in a normal skin area, saline is administered by application of current before administration of an active ingredient by application of current, membrane permeation of the active ingredient is promoted, but the membrane permeability is lower than that in the case of no application of current (Non-Patent Document 1). In contrast, according to the present invention, when an active ingredient is administered through the nipple part by application of current after preliminary treatment, the topical delivery of the active ingredient is considerably increased, as compared with the case of no application of current.

In the present invention, the electrolyte which is topically administered through the nipple part into the mammary gland before administration of an active ingredient may be the one which provides a cationic substance or an anionic substance. Examples of the cationic substances include an alkali metal ion, an alkaline earth metal ion, and an amphoteric ion. Of these, an alkali metal ion is more preferred, and a Na ion or a Li ion is particularly preferred. Examples of the anionic substances include a carbonate ion, a phosphate ion, a halide ion, and an amphoteric ion. Of these, a halide ion is more preferred, and a Cl ion, a Br ion, or a I ion is particularly preferred. Among these electrolytes, an aqueous solution of an alkali metal halide or an alkaline earth metal halide (e.g., NaCl, LiCl, KCl, NaBr, LiBr, KBr, $CaCl_2$, or $CaBr_2$) is particularly preferred, since such an electrolyte acts as both of the cationic substances and the anionic substances.

Examples of the nonsteroidal anti-inflammatory analgesic agent which is an active ingredient of the therapeutic drug for breast cancer and/or mastitis of the present invention include indomethacin, acemetacin, salicylic acid, sodium salicylate, aspirin, acetaminophen, diclofenac sodium, amfenac sodium, ibuprofen, sulindac, naproxen, ketoprofen, flufenamic acid, ibufenac, fenbufen, alclofenac, phenylbutazone, mefenamic acid, bendazac, piroxicam, flurbiprofen, pentazocine, buprenorphine hydrochloride, butorphanol tartrate, celecoxib, rofecoxib, valdecoxib, etoricoxib, lumiracoxib, parecoxib Na, etodolac, NS-398, and meloxicam. Of these, indomethacin or celecoxib is preferred, and indomethacin is particularly preferred, from the viewpoint of effective absorption through the nipple part into the mammary gland.

Examples of the anticancer agent include alkylating agents such as ifosfamide and cyclophosphamide; platinum compounds such as carboplatin, cisplatin, nedaplatin, and oxaliplatin; vegetable anticancer agents such as irinotecan hydrochloride, etoposide, docetaxel hydrate, vincristine sulfate, vinblastine sulfate, paclitaxel, and vinorelbine tartrate; hormones such as tamoxifen citrate, fadrozole hydrochloride hydrate, flutamide, medroxyprogesterone acetate, and miproxifene phosphate; antitumor antibiotics such as doxorubicin hydrochloride, idarubicin hydrochloride, zinostatin stimalamer, daunorubicin hydrochloride, bleomycin hydrochloride, epirubicin hydrochloride, mitoxantrone hydrochloride, pirarubicin hydrochloride, and mitomycin C; antimetabolites such as carmofur, cytarabine, doxifluridine, hydroxycarbamide, methotrexate, mercaptopurine, gemcitabine hydrochloride, fluorouracil, and capecitabine; linear surfactin having a lactone-type cycloheptapeptide structure; and monoclonal antibodies such as trastuzumab. Of these, an alkylating agent such as cyclophosphamide, an antimetabolite such as fluorouracil, or a hormone (antiestrogen) such as tamoxifen citrate or miproxifene phosphate is preferred, and cyclophosphamide, fluorouracil (in particular, 5-fluorouracil), or miproxifene phosphate is particularly preferred, from the viewpoint of effective absorption through the nipple part into the mammary gland.

In the iontophoretic preparation for treatment of breast cancer and/or mastitis of the present invention, which generally includes a donor and a receptor, at least the donor is applied to the nipple part. The iontophoretic preparation generally includes a power supply, an anode (electrode and pad), and a cathode (electrode and pad). The electrode may has, for example, a structure in which the anode and the cathode face each other, or a structure in which the anode (or the cathode) is surrounded by the cathode (or the anode) (Biological Pharmaceutical Bulletin, 26 (4), 518-522, 2003). In this case, when an anionic drug is employed, the cathode is used as a donor, whereas when a cationic drug is employed, the anode is used as a donor. When a nonionic drug is employed, the anode is used as a donor by utilizing the principle of electroosmosis (Biological Pharmaceutical Bulletin, 24, 278-283, 2001; Biological Pharmaceutical Bulletin, 24, 671-677, 2001; and Pharmaceutical Research, 18, 1701-1708, 2001).

Now will be described the donor of the iontophoretic preparation. As shown in FIG. 1, the donor basically includes a support 1, an electrode 2, a pad 3, and a liner 4. Examples of the support include those made of, for example, cotton, polyester, rayon, nylon, polyolefin, polyethylene, vinylon, acetate, polypropylene, polyurethane, and silicone rubber. Examples of the electrode include those made of, for example, carbon, aluminum (including aluminum oxide), stainless steel, gold, silver, copper, silver chloride, platinum, and platinum black. The pad may contain only an electrolyte, only an active ingredient, or both an active ingredient and an electrolyte. An electrolyte and/or an active ingredient may be provided in the form of liquid or gel, and may be applied to the pad or the electrode immediately before treatment with the iontophoretic preparation.

In the present invention, firstly, an electrolyte is topically administered through the nipple part into the mammary gland (i.e., preliminary treatment is carried out), and subsequently, an active ingredient is administered through the nipple part into the mammary gland by application of current. Topical administration of the electrolyte may be carried out through a process of directly injecting a liquid containing the electrolyte through breast ducts; a process of applying a donor containing the electrolyte to the nipple part, followed by delivery of the electrolyte through the nipple part into the mammary gland by application of current; or combination of these processes.

In the process of directly injecting a liquid containing an electrolyte through breast ducts, for example, the electrolyte-containing liquid is injected directly through breast ducts by means of, for example, a microsyringe with a needle having a diameter of 400 to 800 μm. The electrolyte concentration of the electrolyte-containing liquid is preferably 0.01 to 10% by weight, particularly preferably 0.1 to 1.0% by weight, from the viewpoints of improvement of topical delivery of an active ingredient, as well as safety. The solvent employed is preferably, for example, water, hydrous ethanol, or hydrous isopropanol. The dose of the electrolyte-containing liquid is preferably 0.1 to 10.0 mL, particularly preferably 0.5 to 5.0 mL.

In human, the nipple part has about 15 to about 20 breast ducts. When the aforementioned electrolyte-containing liquid is injected, the injection method may vary with the state of a patient or the degree of a disease. For example, injection may be carried out through one breast duct, or may be carried out through a plurality of breast ducts in several portions. When, for example, a stainless steel wire (diameter: 0.25 to 0.35 mm) having a rounded tip is inserted into a breast duct before injection of the electrolyte-containing liquid so as to widen the opening of the duct, the liquid can be injected through the breast duct without causing any damage thereto.

For carrying out the process of applying a donor containing an electrolyte to the nipple part, followed by delivery of the electrolyte through the nipple part into the mammary gland by application of current, a layer containing both an electrolyte and an active ingredient may be provided in a single pad, or an electrolyte-containing layer and an active-ingredient-containing layer may be provided in different pads.

In the former case, both an electrolyte and an active ingredient may be incorporated into a pad initially. Alternatively, only an electrolyte may be incorporated into a pad initially, and an active ingredient may be incorporated into the pad or applied to the surface of the pad after delivery of the electrolyte by application of current. In the present invention, an electrolyte and/or an active ingredient may be applied directly to the nipple part rather than being incorporated into a pad or applied to the surface of the pad, which may be followed by application of current.

In the case where both an electrolyte and an active ingredient are incorporated into a pad initially, when the active ingredient is a cationic substance, an anionic substance is employed as the electrolyte, whereas when the active ingredient is an anionic substance, a cationic substance is employed as the electrolyte. In this case, when current is applied so that the donor serves as a cathode and the receptor serves as an anode, the cationic substance is delivered through the nipple part into the mammary gland, and when current is applied so that the donor serves as an anode and the receptor serves as a cathode, the anionic substance is delivered through the nipple part into the mammary gland. Thus, firstly, the electrolyte can be delivered into the mammary gland, and subsequently, the active ingredient can be delivered into the mammary gland.

In the case where an electrolyte-containing layer and an active-ingredient-containing layer are provided in different pads, preferably, an electrolyte-containing pad is firstly applied to the nipple part, followed by application of current, and an active-ingredient-containing pad is subsequently applied to the nipple part, followed by application of current.

The active-ingredient-containing pad contains a active ingredient, a solvent, an adhesive base, and optionally an electrolyte. Examples of the liner include liners formed of plastic materials such as polyethylene and polypropylene; liners formed of cellulose materials; the aforementioned liners coated with a silicone releasing agent; and paper sheets.

In the present invention, examples of the solvent employed in the pad include water; polyhydric alcohols such as ethylene glycol, diethylene glycol, triethylene glycol, ethylene glycol monoethyl ether, ethylene glycol monobutyl ether, diethylene glycol monomethyl ether, polyethylene glycol, propylene glycol, dipropylene glycol, 1,3-butylene glycol, 2-ethyl-1,3-hexane diol, polypropylene glycol 2000, polypropylene glycol, (concentrated) glycerin, batyl alcohol, pentaerythritol, and D-sorbitol liquid; alcohols such as ethanol, isopropyl alcohol, benzyl alcohol, lauryl alcohol, cetanol, stearyl alcohol, oleyl alcohol, and lanolin alcohol; esters such as diisopropyl adipate, triacetin, diisopropyl sebacate, triisooctanates, and C6 to C12 medium-chain fatty acid triglyceride esters; and ketones such as crotamiton. These solvents may be employed singly or in combination of two or more species.

In the present invention, examples of the adhesive base employed in the pad include water-soluble adhesive bases such as polyacrylic acid, sodium polyacrylate, partially neutralized polyacrylic acid, and N-vinyl acetamide-acrylic acid copolymers; and hydrophobic adhesive bases such as ester gums, alicyclic saturated hydrocarbon resins, aliphatic hydrocarbon resins, polybutene, and rosin. These adhesive bases may be employed singly or in combination of two or more species.

The pad may further contain a base, a thickener, a preservative, a pH adjusting agent, an oil ingredient, a perfume, a stabilizer, a surfactant, a curing agent, or an enhancer.

Examples of the base include sodium alginate, ethylcellulose, carrageenan, carmellose sodium, agar, xanthan gum, gelatin, kaolin, bentonite, montmorillonite, zinc oxide, titanium oxide, silicic anhydride, D-sorbitol, talc, terpene resins, hydroxypropylcellulose, and hydroxypropylmethylcellulose.

Examples of the thickener include carboxyvinyl polymer, urea, polyvinyl alcohol, and sodium metaphosphate.

Examples of the preservative include phenolic substances such as methyl p-hydroxybenzoate, phenol, and cresol; neutral substances such as chlorobutanol and phenylethyl alcohol; invert soaps such as benzalkonium chloride and benzethonium chloride; and acidic substances such as benzoic acid, sorbic acid, dehydro acid, and salicylic acid.

Examples of the pH adjusting agent include citric acid, sodium citrate, hydrochloric acid, glycine, succinic acid, acetic acid, diisopropanolamine, tartaric acid, potassium hydroxide, sodium hydroxide, lactic acid, boric acid, malic acid, phosphoric acid, and borax.

Examples of the oil ingredient include olive oil, camellia oil, castor oil, safflower oil, sunflower oil, sasanqua oil, soybean oil, cottonseed oil, sesame oil, coconut oil, palm oil, and clove oil.

Examples of the perfume include fennel oil, cinnamon oil, clove oil, and peppermint oil.

Examples of the stabilizer include antioxidants such as vitamin E and butylhydroxyanisole; reducing agents such as ascorbic acid, sodium hydrogensulfite, and sodium thiosulfate; and synergistic agents such as sodium citrate, sodium tartrate, lecithin, and EDTA.

Examples of the surfactant include anionic surfactants such as calcium stearate, magnesium stearate, and sodium lauryl sulfate; cationic surfactants such as benzalkonium chloride, benzethonium chloride, and cetylpyridinium chloride; and nonionic surfactants such as glyceryl monostearate, sucrose fatty acid esters, polyoxyethylene hydrogenated castor oil, and polyoxyethylene sorbitan fatty acid esters.

Examples of the curing agent include dried aluminum hydroxide gel, aluminum magnesium hydroxide, magnesium aluminosilicate, magnesium aluminometasilicate, synthetic hydrotalcite, and dihydroxyaluminum aminoacetate.

Examples of the enhancer include nonionic surfactants such as glyceryl monostearate and sucrose fatty acid esters; water-soluble high-molecular-weight compounds such as carboxylic acids; aromatic carboxylic acid compounds such as salicylic acid and derivatives thereof; aliphatic carboxylic acid compounds such as capric acid and oleic acid; terpenes such as L-menthol; esters such as isopropyl myristate and diethyl sebacate; bile acid salts; hydrogenated lanoline; and azone.

The active ingredient content of the pad is preferably 0.001 to 20% by weight, more preferably 0.01 to 10% by weight, from the viewpoint of delivery of the active ingredient through the nipple part into the mammary gland.

The electrolyte concentration of the pad is preferably 0.01 to 10.0% by weight, more preferably 0.05 to 5.0% by weight, particularly preferably 0.1 to 1.0% by weight, from the viewpoints of improvement of delivery of the active ingredient, as well as safety.

In the present invention, the electrolyte and/or the active ingredient may be provided in the form of liquid or gel, and may be applied to the pad or the electrode immediately before application of the donor to the nipple part. In this case, a liquid or gel containing the electrolyte and/or the active ingredient may be prepared by appropriately using ingredients which are incorporated into the pad.

As shown in FIG. 1, the receptor of the iontophoretic preparation for treatment of breast cancer and/or mastitis of the present invention basically includes a support 1, an electrode 2, a pad 3, and a liner 4. The support, electrode, and liner employed in the receptor are similar to those employed in the donor. The pad of the receptor does not contain an active ingredient, but contains an electrolyte.

As shown in WO 98/35722, the iontophoretic preparation may have a structure in which the power supply, the donor, and the receptor are integrated so as to be surrounded by one another, or a structure in which the power supply, the donor, and the receptor are separated so as to face one another.

Figure 2:
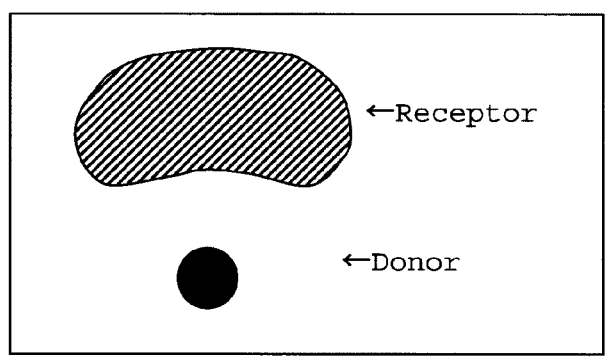
FIG. 2 shows an exemplary form of the donor and the receptor of the iontophoretic preparation for treatment of breast cancer and/or mastitis of the present invention.
Figure 3:
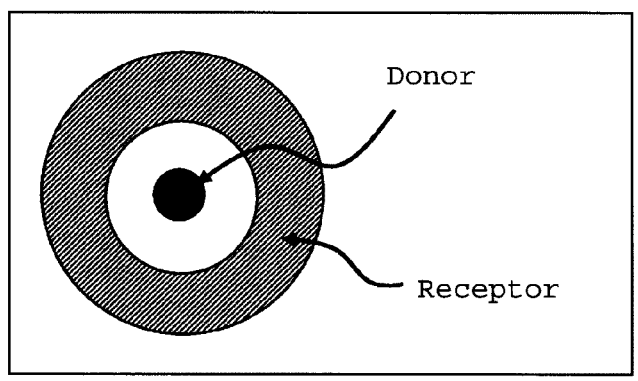
FIG. 3 shows an exemplary form of the donor and the receptor of the iontophoretic preparation for treatment of breast cancer and/or mastitis of the present invention.

In the present invention, preferably, the donor is applied to the nipple part, and the receptor is provided on the breast, from the viewpoint of selective and effective delivery of a nonsteroidal anti-inflammatory analgesic agent and/or an anticancer agent through the nipple part into the mammary gland. In this case, the donor preferably has a size capable of covering the entirety of the nipple part, and the receptor preferably has a size capable of covering at least an affected portion of the breast. No particular limitation is imposed on the form of the donor. However, the donor preferably has a circular or elliptical form, from the viewpoint that it covers the nipple part. The receptor preferably has a circular, elliptical, disk-like, or elliptical disk-like form, from the viewpoint that it covers at least an affected portion of the breast (see FIGS. 2 and 3). Particularly preferably, the receptor has a form so as to cover the entirety of the breast (except for the nipple part); for example, a disk-like form or an elliptical disk-like form (see FIG. 3).

One embodiment of the iontophoretic preparation for treatment of breast cancer and/or mastitis of the present invention includes, as a donor, a pad containing an electrode, an active ingredient, and an electrolyte; and, as a receptor, a pad containing an electrode and an electrolyte. In this embodiment, when the active ingredient is an anionic drug such as indomethacin, a substance which provides a cation (e.g., A Na ion) is incorporated as the electrolyte. When the donor and the receptor are applied to the nipple part and the breast, respectively, and then current is applied so that the donor serves as an anode and the receptor serves as a cathode, electrons flow from the donor (anode) to the receptor (cathode), and, in association with this electron flow, cations contained in the donor migrate into the mammary gland. Subsequently, when current is applied so that the donor serves as a cathode and the receptor serves as an anode, the anionic drug (active ingredient) (e.g., indomethacin) contained in the donor is absorbed into the mammary gland in association with water flow accompanied by migration of cations from the donor (cathode) to the receptor (anode). When the active ingredient is a cationic drug or a nonionic drug, the aforementioned processes are carried out in a reverse manner.

Another embodiment of the iontophoretic preparation of the present invention includes, as a donor, a pad containing an electrode and an electrolyte, and a pad containing an electrode and an active ingredient; and, as a receptor, a pad containing an electrode and an electrolyte. In this embodiment, firstly, the electrolyte-containing pad (i.e., donor) is applied to the nipple part, and the receptor is applied to the breast, followed by application of current. Subsequently, the pad applied to the nipple part is replaced with the active-ingredient-containing pad, and then current is applied again.

Yet another embodiment of the iontophoretic preparation of the present invention includes, as a donor, a pad containing an electrode and an active ingredient; and, as a receptor, a pad containing an electrode. An electrolyte-containing liquid is provided separately from these pads. In this embodiment, the electrolyte-containing liquid is injected directly through breast ducts, and then the donor and the receptor are applied to the nipple part and the breast, respectively, followed by application of current.

EXAMPLES

The present invention will next be described in more detail by way of examples, which should not be construed as limiting the invention thereto.

Japanese Patent No. 4000185 describes that when a donor is applied to the nipple part, and a nonsteroidal anti-inflammatory analgesic agent or an anticancer agent (i.e., an active ingredient) is topically administered through the nipple part into the mammary gland by application of current, the amount of the active ingredient delivered into the mammary gland is remarkably increased. Therefore, in this study, delivery of an active ingredient was examined by means of topical administration of an electrolyte through the nipple part into the mammary gland (i.e., preliminary treatment) by application of current, followed by topical administration of a cationic dye (i.e., a model substance of a cationic drug) in a similar manner.

Example 1

There was performed an in vivo iontophoresis experiment employing a beagle dog, wherein, after preliminary treatment with an aqueous lithium chloride solution, a toluidine blue solution (i.e., cationic dye) was absorbed by application of current.

Specifically, hair was removed from the abdomen of a beagle dog (parous dog, three years old). Thereafter, a donor (formed of a nonwoven fabric sheet having a diameter of 1 cm, and an aluminum foil electrode having the same size as the sheet and stacked thereon) was applied to the nipple part, and a receptor (formed of a doughnut-shaped nonwoven fabric sheet (inner diameter: 2 cm, outer diameter: 5 cm), and an aluminum foil electrode having the same size as the sheet and stacked thereon) was applied to the periphery of the nipple part. For preliminary treatment, the nonwoven fabric sheet of the donor was impregnated with an aqueous solution (200 μL) of 154 mM lithium chloride (product of Wako Pure Chemical Industries, Ltd., lot No. PKH3733), and the nonwoven fabric sheet of the receptor was impregnated with saline (2 mL) (product of Otsuka Pharmaceutical Co., Ltd., lot No. 7D88). Preliminary treatment was carried out by application of current (constant current: 0.1 mA, donor: positive electrode) for five minutes by means of a constant current generator (R6144, product of ADVANTEST). Thereafter, the nonwoven fabric sheet of the donor was removed, and a fresh nonwoven fabric sheet was provided and impregnated with a saline solution (200 μL) containing 0.5% toluidine blue O (product of Chroma, lot No. 281719). Subsequently, current was applied (constant current: 0.1 mA, donor: positive electrode) for 120 minutes in a manner similar to that described above. The beagle dog was killed by bleeding, and then the skin of the nipple part was excised and fixed in formalin. Thereafter, the skin was cut into pieces, followed by embedding and slicing, to thereby prepare a sample. The sample was subjected to image analysis by means of a digital microscope (VHX-600, product of KEYENCE), to thereby determine the depth of delivery of the dye.

Example 2

The procedure of Example 1 was repeated, except that 154 mM lithium chloride (product of Wako Pure Chemical Industries, Ltd., lot No. PKH3733) was replaced with saline (product of Otsuka Pharmaceutical Co., Ltd., lot No. 7D88), to thereby determine the depth of delivery of the dye.

Example 3

Preliminary Treatment by Use of a Solution Containing Both an Electrolyte and a Cationic Dye There was performed an in vivo iontophoresis experiment employing a beagle dog, wherein an aqueous sodium chloride solution containing toluidine blue (i.e., cationic dye) was employed for a donor, and, after preliminary treatment with the sodium chloride solution, the cationic dye was absorbed by application of current (through switching of the direction of current).

Hair was removed from the abdomen of a beagle dog (parous dog, three years old). Thereafter, a donor (formed of a nonwoven fabric sheet having a diameter of 1 cm, and an aluminum foil electrode having the same size as the sheet and stacked thereon) was applied to the nipple part, and a receptor (formed of a doughnut-shaped nonwoven fabric sheet (inner diameter: 2 cm, outer diameter: 5 cm), and an aluminum foil electrode having the same size as the sheet and stacked thereon) was applied to the periphery of the nipple part. The nonwoven fabric sheet of the donor was impregnated with a saline solution (200 μL) containing 0.5% toluidine blue O (product of Chroma, lot No. 281719). The nonwoven fabric sheet of the receptor was impregnated with saline (2 mL) (product of Otsuka Pharmaceutical Co., Ltd., lot No. 7D88). Preliminary treatment was carried out by application of current (constant current: 0.1 mA, donor: negative electrode) for five minutes by means of a constant current generator (R6144, product of ADVANTEST). Thereafter, switching of the direction of current was carried out without exchange of the nonwoven fabric sheet of the donor, and current was applied (constant current: 0.1 mA, donor: positive electrode) for 120 minutes in a manner similar to that described above. The beagle dog was killed by bleeding, and then the skin of the nipple part was excised and fixed in formalin. Thereafter, the skin was cut into pieces, followed by embedding and slicing, to thereby prepare a sample. The sample was subjected to image analysis by means of a digital microscope (VHX-600, product of KEYENCE), to thereby determine the depth of delivery of the dye.

Comparative Example 1

Without Preliminary Treatment Nor Iontophoresis

There was performed an in vivo experiment employing a beagle dog, wherein preliminary treatment with an aqueous electrolyte solution was not carried out, and a toluidine blue solution (i.e., cationic dye) was absorbed without iontophoresis (i.e., without application of current).

Hair was removed from the abdomen of a beagle dog (parous dog, three years old). Thereafter, a donor (formed of a nonwoven fabric sheet having a diameter of 1 cm, and an aluminum foil electrode having the same size as the sheet and stacked thereon) was applied to the nipple part, and a receptor (formed of a doughnut-shaped nonwoven fabric sheet (inner diameter: 2 cm, outer diameter: 5 cm), and an aluminum foil electrode having the same size as the sheet and stacked thereon) was applied to the periphery of the nipple part. The nonwoven fabric sheets were impregnated with a saline solution (200 μL) containing 0.5% toluidine blue O (product of Chroma, lot No. 281719), and then allowed to stand for 120 minutes without application of current. The beagle dog was killed by bleeding, and then the skin of the nipple part was excised and fixed in formalin. Thereafter, the skin was cut into pieces, followed by embedding and slicing, to thereby prepare a sample. The sample was subjected to image analysis by means of a digital microscope (VEX-600, product of KEYENCE), to thereby determine the depth of delivery of the dye.

Comparative Example 2

Without Preliminary Treatment

There was performed an in vivo iontophoresis experiment employing a beagle dog, wherein preliminary treatment with an aqueous electrolyte solution was not carried out, and a toluidine blue solution (i.e., cationic dye) was absorbed by application of current.

The procedure of Comparative Example 1 was repeated, except that current was applied (constant current: 0.1 mA, donor: positive electrode) for 120 minutes after impregnation with the toluidine blue solution, to thereby determine the depth of delivery of the dye.

Comparative Example 3

Without Iontophoresis

The procedure of Comparative Example 1 was repeated, except that preliminary treatment was carried out in a manner similar to that described in Example 2, and then the nonwoven fabric sheets impregnated with the saline solution were allowed to stand for 120 minutes without application of current, to thereby determine the depth of delivery of the dye.

Table 1 shows the results of Examples 1 to 3 and Comparative Examples 1 to 3.

TABLE 1

| Preliminary treatment* | Exchange of nonwoven fabric | Application of current | Ion species used for preliminary treatment | Delivery depth (mm) | Ratio to control | Examples and Comparative Examples |
|---|---|---|---|---|---|---|
| Not done | Done | Not done (Passive) | | 0.43 | 0.78 | Comparative Example 1 |
| | Done | Done | | 0.55 | as 1 | Comparative Example 2 |
| Done | Done | Not done (Passive) | Na | 0.44 | 0.80 | Comparative Example 3 |
| | Done | Done | Na | 1.06 | 1.93 | Example 2 |
| | Done | | Li | 1.44 | 2.62 | Example 1 |
| | Not done | | Cl | 0.84 | 1.53 | Example 3 |

*time: 5 minutes - current: 0.1 mA

As is clear from data shown in Table 1, when an electrolyte is topically administered through the nipple part into the mammary gland by application of current (i.e., preliminary treatment is carried out), and then an active ingredient is topically administered through the nipple part into the mammary gland in a similar manner, the active ingredient is rapidly and effectively delivered into a deep portion of the mammary gland, as compared with the case where preliminary treatment is not carried out.

Example 4

Hair was removed from the nipple part and the breast of a beagle dog (parous dog, six years old). Thereafter, a stainless steel wire having a rounded tip (0.25 to 0.35 mm, product of Natsume Seisakusho Co., Ltd.) was inserted into a breast duct, and the opening of the breast duct was widened by gradually increasing the diameter of the stainless steel wire (hereinafter this process will be referred to as "duct-widening process"). This duct-widening process was carried out for four breast ducts of one nipple part.

After completion of the duct-widening process, all the thus-treated breast ducts were washed by injecting saline (0.9% aqueous sodium chloride solution) into the breast ducts by means of a Hamilton syringe (200 μL) (i.e., preliminary treatment), and then squeezing liquid from the ducts by massage. Thereafter, there was performed an in vivo experiment, in which a toluidine blue solution (i.e., cationic dye) was absorbed by application of current. In this experiment, a donor (formed of a nonwoven fabric sheet having a diameter of 1 cm, and an aluminum foil electrode having the same size as the sheet and stacked thereon) was applied to the nipple part, and a receptor (formed of a doughnut-shaped nonwoven fabric sheet (inner diameter: 2 cm, outer diameter: 5 cm), and an aluminum foil electrode having the same size as the sheet and stacked thereon) was applied to the periphery of the nipple part. The nonwoven fabric sheets were impregnated with a saline solution (200 μL) containing 0.5% toluidine blue 0 (product of Chroma, lot No. 281719), followed by application of current (constant current: 0.1 mA, donor: positive electrode) for 120 minutes. During application of current, voltage was measured by means of a voltage recorder (Memory HiCorder 8807, product of Hioki E. E. Corporation) for determination of electrical resistance. The beagle dog was killed by bleeding, and then the skin of the nipple part was excised and fixed in formalin. Thereafter, the skin was cut into pieces, followed by embedding and slicing, to thereby prepare a sample. The sample was subjected to image analysis by means of a digital microscope (VHX-600, product of KEYENCE), to thereby determine the depth of delivery of the dye.

Comparative Example 4

In a manner similar to that described in Example 4, the nipple part was subjected to a duct-widening process. A suction cup of a breast pump was applied to the nipple part, and suction treatment was carried out for 10 to 15 seconds. After completion of suction treatment, in a manner similar to that described in Example 4, an experiment (absorption of a toluidine blue solution (i.e., cationic dye) by application of current) was carried out, and the depth of delivery of the dye and electrical resistance were determined.

Comparative Example 5

Without performing preliminary treatment, in a manner similar to that described in Example 4, the nipple part was subjected to a duct-widening process and then to an experiment (absorption of a toluidine blue solution (i.e., cationic dye) by application of current), and the depth of delivery of the dye and electrical resistance were determined.

Table 2 shows the results of Example 4 and Comparative Examples 4 and 5.

TABLE 2

| Examples and Comparative Examples | Electrical resistance (kΩ) | Delivery depth (mm) | Ratio to control |
|---|---|---|---|
| Comparative Example 5 | 84 | 3.52 | as 1 |
| Example 4 | 24 | 7.96 | 2.26 |
| Comparative Example 4 | 4 | 0.91 | 0.26 |

As shown in Table 2, the depth of delivery of the dye was increased by carrying out preliminary treatment (Example 4). In contrast, in the case of a simple suction treatment, the depth of delivery of the dye was decreased, although electrical resistance was considerably reduced (Comparative Example 4).

These data showed that topical administration of an electrolyte through the nipple part into the mammary gland (i.e., preliminary treatment) is effective for iontophoretic therapy of breast cancer and/or mastitis.

The invention claimed is:

1. An iontophoretic therapy method for breast cancer and/or mastitis, which comprises:
   topically administering an electrolyte through a nipple part into a mammary gland;
   subsequently applying, to the nipple part, a donor comprising, as an active ingredient, a nonsteroidal anti-inflammatory analgesic agent and/or an anticancer agent; and
   topically administering the active ingredient through the nipple part into the mammary gland by application of current.

2. The method according to claim 1, wherein the topically administering of the electrolyte through the nipple part into the mammary gland is carried out by applying a donor comprising the electrolyte to the nipple part, and delivering the electrolyte through the nipple part into the mammary gland by application of current.

3. The method according to claim 1, wherein the topically administering of the electrolyte through the nipple part into the mammary gland is carried out by directly injecting a liquid comprising the electrolyte through a breast duct.

4. The method according to claim 1, wherein the electrolyte is a substance which comprises a Na ion, a Li ion, or a Cl ion.

5. The method according to claim 2, wherein the electrolyte is a substance which comprises a Na ion, a Li ion, or a Cl ion.

6. The method according to claim 3, wherein the electrolyte is a substance which comprises a Na ion, a Li ion, or a Cl ion.

7. The method according to claim 1, which is for breast cancer therapy.

8. The method according to claim 1, which is for mastitis therapy.

9. The method according to claim 8, wherein the active ingredient is a nonsteroidal anti-inflammatory analgesic agent.

10. The method according to claim 7, wherein the active ingredient is an anticancer agent.

* * * * *